(12) United States Patent
Pascal

(10) Patent No.: US 9,730,573 B2
(45) Date of Patent: Aug. 15, 2017

(54) NARROW BAND IN-VIVO IMAGING DEVICE

(75) Inventor: Amit Pascal, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 2493 days.

(21) Appl. No.: 11/723,500

(22) Filed: Mar. 20, 2007

(65) Prior Publication Data

US 2008/0234548 A1 Sep. 25, 2008

(51) Int. Cl.
*A61B 1/06* (2006.01)
*A61B 1/04* (2006.01)

(52) U.S. Cl.
CPC .......... *A61B 1/041* (2013.01); *A61B 1/0638* (2013.01)

(58) Field of Classification Search
CPC .............................. A61B 1/0638; A61B 1/041
USPC ........... 600/160, 167, 407, 424, 476
See application file for complete search history.

(56) References Cited

U.S. PATENT DOCUMENTS

| | | | |
|---|---|---|---|
| 3,971,065 A | 7/1976 | Bayer | |
| 4,290,844 A * | 9/1981 | Rotolante et al. | 438/66 |
| 5,604,531 A | 2/1997 | Iddan et al. | |
| 5,749,830 A * | 5/1998 | Kaneko et al. | 600/160 |
| 6,222,189 B1 | 4/2001 | Misner et al. | |
| 6,659,940 B2 * | 12/2003 | Adler | 600/109 |
| 7,009,634 B2 | 3/2006 | Iddan et al. | |
| 7,347,817 B2 | 3/2008 | Glukhovsky et al. | |
| 2001/0017649 A1 * | 8/2001 | Yaron | 348/45 |
| 2003/0120130 A1 * | 6/2003 | Glukhovsky et al. | 600/109 |
| 2003/0208107 A1 * | 11/2003 | Refael | 600/300 |
| 2003/0223248 A1 | 12/2003 | Cronin et al. | |
| 2004/0056966 A1 | 3/2004 | Schechner et al. | |
| 2004/0066547 A1 | 4/2004 | Parker et al. | |
| 2004/0158300 A1 * | 8/2004 | Gardiner | 607/88 |
| 2005/0187433 A1 | 8/2005 | Horn et al. | |
| 2006/0149132 A1 | 7/2006 | Iddan | |

FOREIGN PATENT DOCUMENTS

| | | |
|---|---|---|
| EP | 1 326 432 | 7/2003 |
| WO | WO 2004/054430 | 7/2004 |
| WO | WO 2007/004227 | 1/2007 |

OTHER PUBLICATIONS

International Search Report of Application No. PCT/IL08/00387 mailed on Nov. 26, 2008.
Supplementary Search Report for European Application No. EP 08 72 0012 dated Nov. 30, 2010.

\* cited by examiner

*Primary Examiner* — Joseph M Santos Rodriguez
(74) *Attorney, Agent, or Firm* — Pearl Cohen Zedek Latzer Baratz LLP

(57) ABSTRACT

An in-vivo imaging device for capturing one or more narrow band images of the gastrointestinal tract, or other body lumens or cavities of a patient, using one or more narrow band illumination sources and an imager having an array of light sensitive elements.

25 Claims, 3 Drawing Sheets

NARROW BAND IN-VIVO IMAGING DEVICE

FIELD OF THE INVENTION

The present invention relates to a narrow band in-vivo imaging device having an imager capable of capturing more than one narrow band image.

BACKGROUND OF THE INVENTION

In-vivo imaging devices such as, for example, ingestible imaging capsules, for imaging of the gastrointestinal (GI) tract or other body lumens of a patient may wirelessly transmit image data to an external data recorder. The data recorder may be affixed to the patient by a strap or a belt so that the patient may freely perform normal actions during an observation period that may begin after swallowing the in-vivo imaging device and end upon its excretion. The data recorder may have radio communication capability and it may have connected to it one or more antennas for receiving the image data transmitted by the in-vivo imaging device and the data recorder may have a memory for storing the received image data. After the observation period, the patient may deliver the data recorder to an operator, for example, a health professional who may download the stored image data for processing and for performing analysis of the GI tract for diagnosis purposes.

The image data includes images of the GI tract captured by an imager in the in-vivo imaging device as it passes through the GI tract. The image data may be downloaded from the data recorder to a workstation, or the like, where it may undergo various forms of image processing prior to analysis of the images of the GI tract for diagnosis purposes. The images may be obtained using illumination sources of light radiation, for example, light emitting diodes (LEDs), which may be located in the in-vivo imaging devices. Emitted light radiation may illuminate target areas of the GI tract, or other body lumens, and light radiation may be reflected back from the target areas to the imager in the in-vivo imaging device thereby producing images of the target areas. The imager may be any array of light sensitive elements, for example a charge coupled device (CCD), and the illumination sources may be broad spectrum white light sources. Colored images may be obtained by using an imager with colored filters covering its light sensitive elements. For example, red, green and blue filters may be used. The color filters may be designed to be relatively broadband in order to reduce intensity loss of light passing through them. It is sometimes required to perform narrow band imaging. For example, using a red light illumination source. In such cases, an imager sensitive to the red light illumination is used. Such an imager cannot be used for two different types of narrow band illumination sources, for example for both a red and a blue light illumination source.

SUMMARY OF THE INVENTION

In accordance with some embodiments of the present invention, there is provided an in vivo imaging device for providing at least first and second images of an in-vivo target area, the in-vivo imaging device comprising:

first and second types of illumination source of light radiation for simultaneously illuminating the target area and giving rise to reflected radiation therefrom, the first and second types of illumination source having differing first and second illumination spectra; and an imager for simultaneously receiving the radiation reflected from the target area by illumination from the first and second types of illumination source, the imager comprising an array of first and second types of light sensitive elements having differing first and second sensitivity spectra, the first and second types of light sensitive element being responsive to illumination spectra having spectral regions overlapping at least partially with the first and second sensitivity spectra, respectively, the first image being obtained from the first light sensitive elements and the second image being obtained from the second light sensitive elements; wherein the first sensitivity spectrum at least partially overlaps the first illumination spectrum by a first area of overlap A11, and the second sensitivity spectrum at least partially overlaps the second illumination spectrum by a second area of overlap A22.

In accordance with some embodiments of the present invention, the sensitivity spectrum of the first type of light sensitive element partially overlaps the sensitivity spectrum of the second type of light sensitive element.

In accordance with some embodiments of the present invention, the first sensitivity spectrum partially overlaps the second illumination spectrum by a third area of overlap A12.

In accordance with some embodiments, the second sensitivity spectrum partially overlaps the first illumination spectrum by a fourth area of overlap A21.

In accordance with some embodiments, the first area of overlap A11 is greater or equal to five times the third area of overlap A12.

In accordance with some embodiments, the second area of overlap A22 is greater or equal to five times the fourth area of overlap A21.

In accordance with some embodiments of the present invention, the in vivo imaging device further comprises a third type of illumination source of light radiation for illuminating the target area simultaneously with the first and second types of illumination source and giving rise to reflected radiation therefrom, the third type of illumination source having a third illumination spectrum differing from the first and second illumination spectra, the imager for simultaneously receiving the radiation reflected from the target by illumination from the first, second and third types of illumination source, and the array further comprising a third type of light sensitive element having a third sensitivity spectrum differing from the first and second sensitivity spectra, the third type of light sensitive element being responsive to illumination spectra having spectral regions overlapping at least partially with the third sensitivity spectrum, the third sensitivity spectrum at least partially overlaps the third illumination spectrum by a fifth area of overlap A33 and a third image is obtained from the third light sensitive elements.

In accordance with some embodiments, the third sensitivity spectrum partially overlaps the second illumination spectrum by a sixth area of overlap A32.

In accordance with some embodiments, the fifth area of overlap A33 is greater or equal to five times the sixth area of overlap A32.

In accordance with some embodiments of the present invention, the array is a planar array.

In accordance with some embodiments of the present invention, the array is a mosaic array.

In accordance with some embodiments of the present invention, the light sensitive elements are arranged in groups of four.

In accordance with some embodiments of the present invention, each group comprises four adjacent light sensitive elements made up of two green light sensitive elements, one red light sensitive element and one blue light sensitive element.

In accordance with some embodiments of the present invention, the illumination spectrum of the first type of illumination source has a first illumination full width half maximum (FWHM) and the sensitivity spectrum of the first type of light sensitive element has a first sensitivity FWHM, the first illumination FWHM being less than the first sensitivity FWHM.

In accordance with some embodiments of the present invention, the illumination spectrum of the second type of illumination source has a second illumination FWHM and the sensitivity spectrum of the second type of light sensitive element has a second sensitivity FWHM, the second illumination FWHM being less than the second sensitivity FWHM.

In accordance with some embodiments of the present invention, the in-vivo imaging device further comprises a third type of illumination source and a third type of light sensitive element, the third type of illumination source having an illumination spectrum differing from the illumination spectrums of the first and second types of illumination sources, the third type of light sensitive element having an sensitivity spectrum differing from the sensitivity spectrums of the first and second types of light sensitive element, wherein the illumination spectrum of the third type of illumination source has a third illumination FWHM and the sensitivity spectrum of the third type of light sensitive element has a third sensitivity FWHM, the third illumination FWHM being less than the third sensitivity FWHM.

In accordance with some embodiments of the present invention, the illumination spectrum of the first type of illumination source has a first illumination center wavelength and the sensitivity spectrum of the first type of light sensitive element has a first sensitivity center wavelength, the first illumination center wavelength being less than the first sensitivity center wavelength.

In accordance with some embodiments of the present invention, the illumination spectrum of the second type of illumination source has a second illumination center wavelength and the sensitivity spectrum of the second type of light sensitive element has a second sensitivity center wavelength, the second illumination center wavelength being greater than the second sensitivity center wavelength.

In accordance with some embodiments of the present invention, the in vivo imaging device further comprises a third type of illumination source and the array further comprises a third type of light sensitive element, the third type of illumination source having an illumination spectrum differing from the illumination spectrums of the first and second types of illumination sources, the third type of light sensitive element having an sensitivity spectrum differing from the sensitivity spectrums of the first and second types of light sensitive element, wherein the illumination spectrum of the third type of illumination source has a third illumination center wavelength and the sensitivity spectrum of the third type of light sensitive element has a third sensitivity center wavelength, the third illumination center wavelength being greater than the third sensitivity center wavelength. In accordance with some embodiments of the present invention there is provided an in-vivo imaging device for narrow band imaging comprising:

a plurality of narrow band illumination sources; and an imager comprising a plurality of light sensitive elements arranged in a mosaic array for capturing a plurality of narrow band images simultaneously.

BRIEF DESCRIPTION OF THE DRAWINGS

The present invention will be understood and appreciated more fully from the following detailed description taken in conjunction with the drawings in which.

Figure 1:
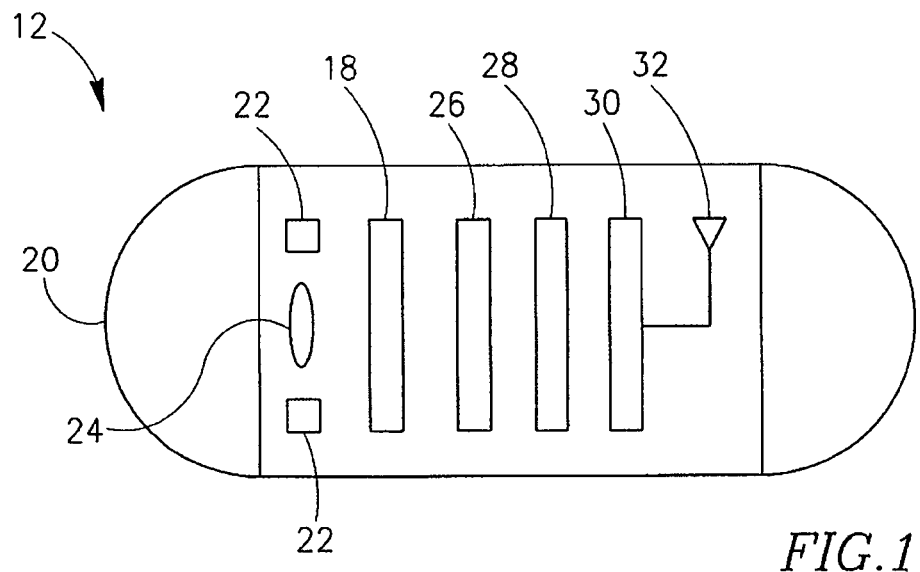
FIG. 1 is a simplified illustrative side view of an in-vivo imaging device according to embodiments of the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

The device of the present invention may be used with an imaging system or device such as that described in U.S. Pat. No. 5,604,531 entitled "In Vivo Video Camera System," which is incorporated herein by reference. A further example of an imaging system and device with which the device of the present invention may be used is described in U.S. Pat. No. 7,009,634 entitled "Device for In Vivo Imaging," which is incorporated herein by reference. For example, a swallowable imaging capsule such as that described in U.S. Pat. No. 7,009,634, may be used in the present invention. A further example of swallowable imaging capsules that may be used with the device of the present invention are those described in U.S. Patent Application Publication No. 2005/0187433 entitled "In-vivo Imaging Device Providing Constant Bit Rate Transmission," which is incorporated herein by reference. Yet a further example of swallowable imaging capsules that may be used with the device of the present invention are those described in U.S. Patent Application Publication No. 2006/0036131 entitled "In vivo imaging device, system and method," which is incorporated herein by reference.

Reference is made to FIG. 1, showing an in-vivo imaging device 12 according to embodiments of the present invention. In some embodiments, the in-vivo imaging s device 12 may be a wireless device. In some embodiments, the in-vivo imaging device 12 may be autonomous. In some embodiments, the in-vivo imaging device 12 may be a swallowable capsule for imaging the gastrointestinal (GI) tract of a patient. However, other body lumens or cavities may be imaged or examined with the in-vivo imaging device 12.

The in-vivo imaging device 12 may be generally cylindrical in shape with dome-like ends and may include at least one imager 18 for capturing image data of the gastrointestinal tract or other body lumens or cavities, a viewing window 20 at at least one of the ends, one or more illumination sources 22, an optical system 24, a power supply such as a battery 26, a processor 28, a transceiver 30, and an antenna 32 connected to the transceiver 30. As the in-vivo imaging device 12 traverses the gastrointestinal tract or other body lumens of a patient, it takes a series of images thereof. The illumination sources 22 may be Light Emitting Diodes (LED) or other suitable illumination sources for illuminating a target area from which images are to be captured. The target area may be an area of the gastrointestinal tract or other body lumens or cavities of the patient.

The imager 18 of the in-vivo imaging device 12 may capture series of images to form a data stream, forming the frames of a video movie. The imager 18 may be and/or may contain a CMOS imager. Alternatively, other imagers may be used, e.g. a CCD imager or other imagers. The image data and or other data captured by the in-vivo imaging device 12 may be transmitted as a data signal by wireless connection, e.g. by a wireless communication channel, by the transceiver 30 via the antenna 32, from the in-vivo imaging device 12 and received by an external recorder.

When viewing certain lumens or cavities; it may be advantageous to use various different types of illumination sources. In some embodiments, the illumination sources 22 may be broad band white light illumination sources for obtaining color images of a target area. In some embodiments, the illumination sources 22 may be narrow band illumination sources for obtaining narrow band images of a target area. In some embodiments, the narrow band illumination sources may be colored light illumination sources, including, for example, red, green and blue illumination sources for obtaining, respectively, red, green and blue narrow band images of a target area. In some embodiments, the narrow band illumination sources may include infra-red and ultra-violet illumination sources.

In some embodiments all of the illumination sources 22 may be the same, or substantially the same, that is, they all may have the same, or substantially the same spectrum of illumination. In other embodiments some or all of the illumination sources may be different, that is, may have different spectra of illumination. Each of the illumination sources 22 may be, for example, an individual source, such as a lamp or a LED, or may be sets of illumination sources, arranged in a certain configuration such as a ring of LEDs that may be arranged, for example, around optical system 24. The in-vivo illumination sources 22 may be located at, or proximal to, at least one end of the in-vivo imaging device 12. According to other embodiments, the illumination sources 22 need not be located at an end of the in-vivo imaging device 12. Rather they may illuminate through a side window or a window located at another location.

Figure 2:
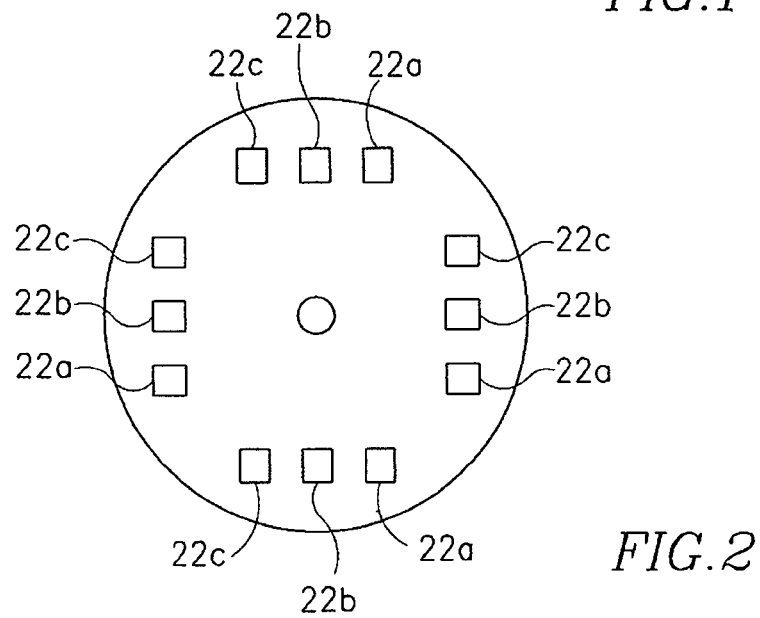
FIG. 2 is an illustrative end view of an in-vivo imaging device in accordance with embodiments of the present invention.

Reference is now made to FIG. 2, showing an illustrative end view of the in-vivo imaging device 12 in accordance with embodiments of the present invention. The illumination sources 22 may be arranged in groups. In some embodiments, each group may contain narrow band illumination sources, such as for example a red light illumination source 22*a*, a green light illumination source 22*b* and a blue light illumination source 22*c*. In the embodiment illustrated in FIG. 2 there are four groups, each group containing three narrow band illumination sources 22*a*, 22*b*, 22*c*.

Figure 3:
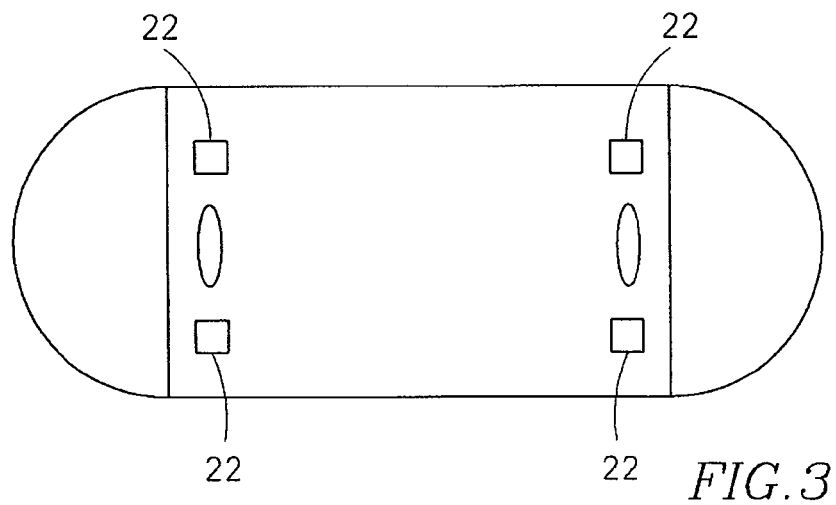
FIG. 3 is a simplified illustrative side view of an in-vivo imaging device with illumination sources at both ends.

Reference is now made to FIG. 3, showing an illustrative schematic side view of the in-vivo imaging device 12 with illumination sources 22 at both ends or proximal to both ends in accordance with some embodiments of the present invention. Having illumination sources 22 at both of its ends, allows the in-vivo imaging device 12 to capture images in both forward and rearward directions, relative to the direction of motion, as it traverses the gastrointestinal tract or other body lumens of a patient. The illumination sources 22 proximal to one end of the in-vivo imaging device 12 may be narrow band colored illumination sources and the illumination sources 22 proximal to the other end may be wide band white illumination sources. In some embodiments, in-vivo imaging device 12 may have narrow band illumination sources proximal to both ends.

Figure 4:
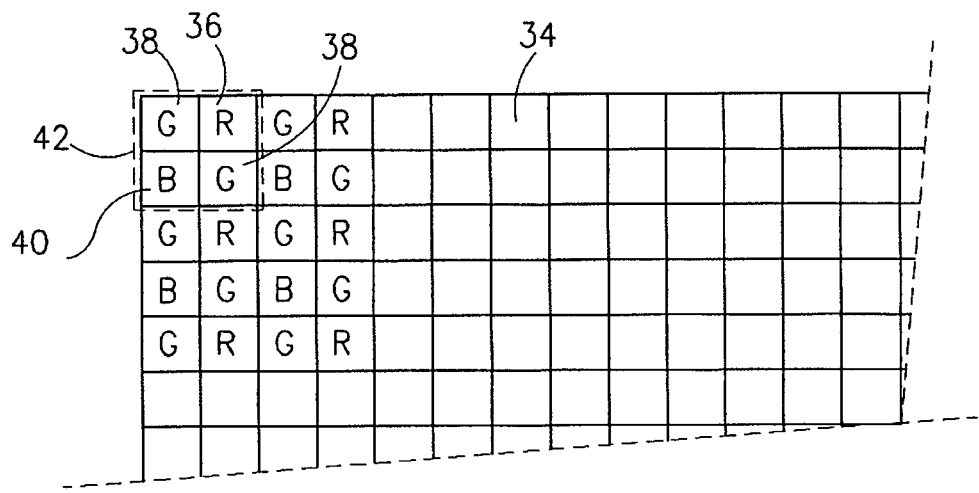
FIG. 4 shows an illustrative example of a mosaic pixel arrangement of an imager according to embodiments of the present invention.

Reference is now made to FIG. 4, showing an illustrative example of a mosaic pixel arrangement of the imager 18 in accordance with embodiments of the present invention. The imager 18 may include an array of sensors or light sensitive elements 34. The light sensitive elements 34 may be covered by wavelength sensitive filters. In accordance with some embodiments, there may be at least two types of light sensitive elements 34, each type of light sensitive element having a different sensitivity spectrum (or spectral response, or quantum efficiency). In accordance with some embodiments, there may be three types of light sensitive elements 34. Each of the three types of light sensitive elements may have a different sensitivity spectrum, that is, they may each be sensitive to different wavelength bands of the electromagnetic spectrum. For example, one type of light sensitive element may be a red light sensitive element 36, sensitive to red light radiation, another type of light sensitive element may be a green light sensitive element 38, sensitive to green light radiation and another type of light sensitive element may be a blue light sensitive element 40, sensitive to blue light radiation. Such a mosaic pixel arrangement may be referred to as an RGB color pixel arrangement, and the corresponding imager an RGB sensor array. The particular RGB color pixel arrangement illustrated in FIG. 4 is known as a Bayer pattern. Other mosaic pixel arrangements may be used. Other colors may also be used. For example, cyan, magneta, yellow and green light sensitive elements may be used (also referred to as a CMYG color pixel arrangement, or CMYG sensor array).

Using a an imager having a mosaic pixel arrangement such as, for example, that shown in FIG. 4, the in-vivo imaging device 12 may be used for narrow band imaging as well as for wide band imaging. Broad band white light illumination sources may be used to obtain color images. In accordance with some embodiments, color images may be obtained by arranging the color light sensitive elements 36, 38, 40 in groups of four light sensitive elements. For example, as shown in FIG. 4, each group 42 may comprise four adjacent light sensitive elements made up of two green light sensitive elements 38, one red light sensitive element 36 and one blue light sensitive element 40 (see, for example, U.S. Pat. No. 3,971,065 entitled "Color Imaging Array,").

Figure 5A:
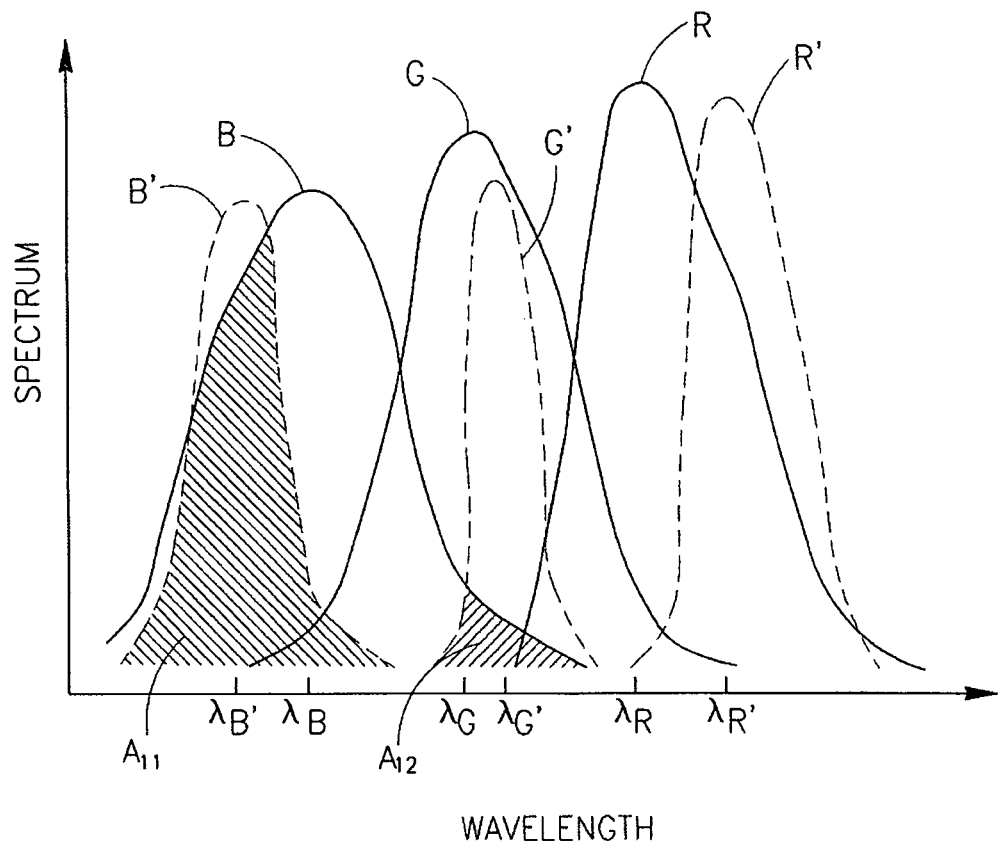
FIGS. 5A to 5C show illustrative examples of red, green and blue spectra and areas of overlap according to embodiments of the invention.
Figure 5B:
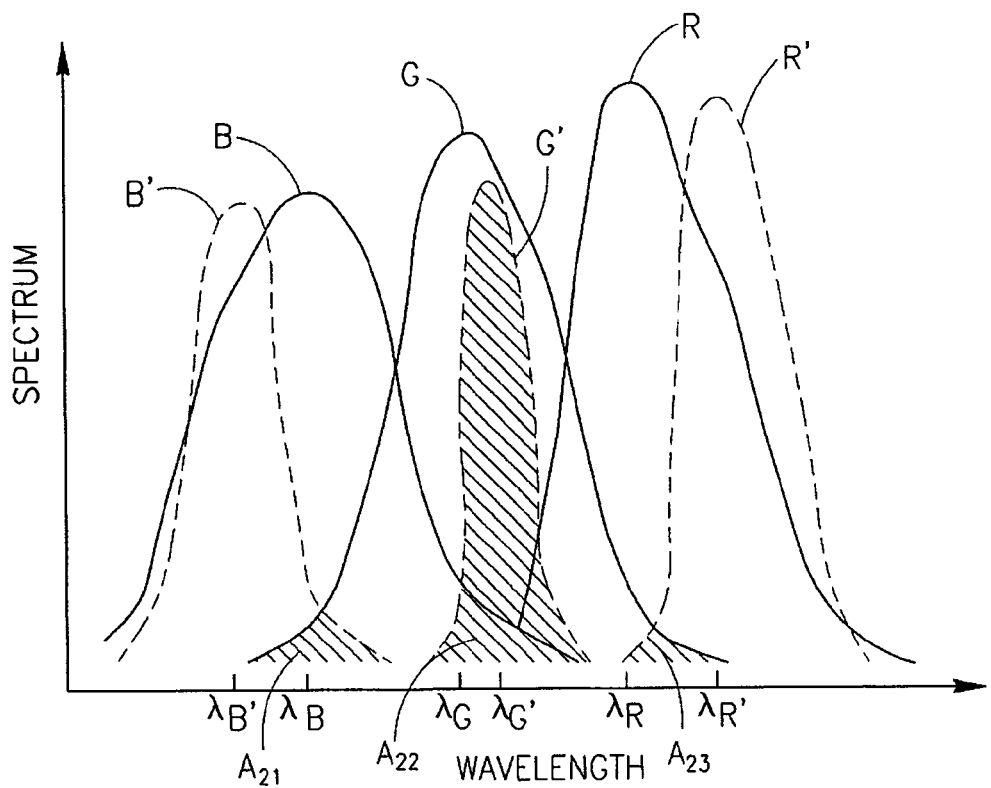
Figure 5C:
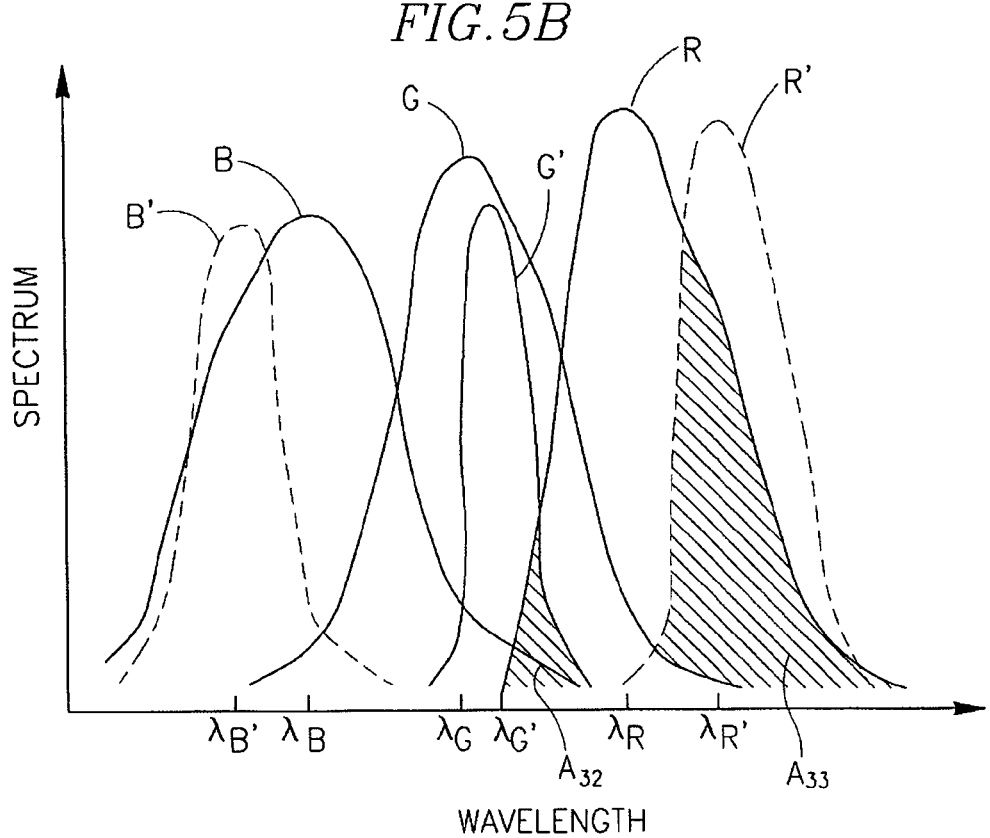

Reference is now made to FIGS. 5A to 5C showing illustrative examples of various red, green and blue spectra according to some embodiments of the invention. The curves drawn with continuous lines represent illustrative examples of the sensitivity spectra R, G, B, of red green and blue light sensitive elements, respectively. For example, the sensitivity spectra R, G, B, may be the sensitivity spectra of the red green and blue light sensitive elements 36, 38, 40, which may be used for the mosaic pixel arrangement of the imager 18 shown in FIG. 4.

The curves drawn with dashed lines represent illustrative examples of the illumination spectra R', G', B' of narrow band red, green and blue illumination sources, respectively. Fore example, the illumination spectra R', G', B' may be the illumination spectra of the red, green and blue illumination sources 22a, 22b, 22c, respectively, shown in FIG. 2.

As can be seen in FIGS. 5A to 5C, the sensitivity spectra R, G, B may be relatively broadband and may partially overlap. In a non-binding example, in accordance with some embodiments, the center wavelengths of the sensitivity spectra R, G and B may be $\lambda_R$=600 nm, $\lambda_G$=540 nm and $\lambda_B$=460 nm, respectively, and their full width half maximum (FWHM) may be 100 nm, 80 nm and 80-100 nm, respectively.

As can further be seen in FIG. 5, the illumination spectra R', G', B' of the illumination sources may be relatively narrow band and may preferably not overlap. In a non-binding example, in accordance with some embodiments, the center wavelengths of the illumination spectra R', G' and B' may be $\lambda R_{'}$=550 nm, $\lambda_{B_{'}}$=555 nm and $\lambda_{B_{'}}$=425 nm, respectively, and their FWHM may be 30 nm, 20 nm and 50 nm, respectively.

By comparing the FWHM of the various spectra, it is seen that in accordance with the above examples of some embodiments, the red sensitivity spectrum R is broader than its associated red illumination spectrum R' (100>30), the green sensitivity spectrum G is broader than its associated green illumination spectrum G' (80>20) and the blue sensitivity spectrum B is broader than its associated blue illumination spectrum B' (80-100>50).

As can yet further be seen in FIGS. 5A to 5C, the value of the center wavelength $\lambda_{R'}$ and of the FWHM of the red illumination spectrum R' may chosen so that on the one hand there is as large as possible overlap (A33) between the red sensitivity spectrum R and its associated red illumination spectrum R' and on the other hand as little as possible overlap (A32) between the red sensitivity spectrum R and any other illumination spectrum, for example the green illumination spectrum G'. Consequently, the red light sensitive element 36 is responsive mainly to its associated red illumination spectrum R'. Similarly, the value of the center wavelength $\lambda_{G'}$ and of the FWHM of the green illumination spectrum G' may chosen so that on the one hand there is as large as possible overlap (A22) between the green sensitivity spectrum G and its associated green illumination spectrum G' and on the other hand as little as possible overlap between the green sensitivity spectrum G and any other illumination spectra, for example, overlap (A23, A21) with the red and blue illumination spectra R' and B'. Consequently, the green light sensitive element 38 is responsive mainly to its associated green illumination spectrum G'. Similarly, the value of the center wavelength $\lambda_{B'}$ and of the FWHM of the blue illumination spectrum B' may chosen so that on the one hand there is as large as possible overlap (A11) between the blue sensitivity spectrum B and its associated blue illumination spectrum B' and on the other hand as little as possible overlap between the blue sensitivity spectrum B and any other illumination spectra, for example, overlap (A12) with the green illumination spectrum G'. Consequently, the blue light sensitive element 40 is responsive mainly to its associated blue illumination spectrum B'.

The overlap between a given sensitivity spectrum and any illumination spectrum is representative of the imaging signal captured by the light sensitive element having the given sensitivity spectrum. In general, the imaging signal captured by a given light sensitive element will have a main contribution resulting from the overlap between the given color sensitivity spectrum and its associated color illumination spectrum and a minor contribution resulting from the overlap between the given color sensitivity spectrum and other color illumination spectra. For example, the overlap area A11 in FIG. 5A is representative of the main contribution to a blue narrow band imaging signal captured by the imager due to the overlap of the blue sensitivity spectrum B and its associated blue illumination spectrum B'. The overlap area A12 is representative of a minor contribution to the blue narrow band imaging signal due to the overlap of the blue sensitivity spectrum B with the green illumination spectrum G'. This minor contribution, which may be considered as a broad band contribution, may be regarded as noise, which should preferably be kept to a minimum by suitably designing the illumination sources relative to the sensitivity spectra of the light sensitive elements of the imager. This may be achieved by appropriate choice of the center wavelengths and the FWHM of the illumination spectra of the illumination sources. In accordance with some embodiments of the present invention the signal to noise ratio, that is, the ratio of the overlap areas of the major to minor contributions to the captured imaging signal should be greater or equal to 5.

In accordance with some embodiments, two or more narrow band images of a given target area may be obtained simultaneously from the same imager. The imager having a mosaic pixel arrangement as described herein.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the scope of the invention.

What is claimed is:

1. An in-vivo imaging device for providing at least first and second narrow band images of an in-vivo target area, the in-vivo imaging device comprising:

a first type and a second type of narrow band illumination sources of light radiation for simultaneously illuminating the target area and giving rise to reflected radiation therefrom, the first and second types of illumination sources having non-overlapping first and second illumination spectra; and an imager to simultaneously capture said at least first and second images based on simultaneously receiving the radiation reflected from the target area by illumination from the first and second types of illumination sources, the imager comprising an array of a first and a second types of light sensitive elements covered by wavelength sensitive filters and having differing first and second sensitivity spectra, the first and the second types of light sensitive elements being responsive to the first and the second illumination spectra, respectively, wherein values of full width half maximum (FWHM) of the first and the second illumination spectra are less than values of FWHM of the first and the second sensitivity spectra, respectively, wherein values of center wavelength and of FWHM of the first illumination spectrum are such that an overlap between the first sensitivity spectrum and the first illumination spectrum is larger than an overlap between the first sensitivity spectrum and the second illumination spectrum, and wherein values of center wavelength and of FWHM of the second illumination spectrum are such that an overlap between the second sensitivity spectrum and the second illumination spectrum is larger than an overlap between the second sensitivity spectrum and the first illumination spectrum.

2. The in-vivo imaging device according to claim 1, wherein the overlap between the first sensitivity spectrum and the first illumination spectrum-is greater or equal to five times the overlap between the first sensitivity spectrum and the second illumination spectrum.

3. The in-vivo imaging device according to claim 1, wherein the overlap between the second sensitivity spectrum and the second illumination spectrum is greater or equal to five times the overlap between the second sensitivity spectrum and the first illumination spectrum.

4. The in-vivo imaging device according to claim 1, further comprising:
   a third type of narrow band illumination source of light radiation for illuminating the target area simultaneously with the first and second types of illumination source and giving rise to reflected radiation therefrom, the third type of illumination source having a third illumination spectrum non-overlapping the first and second illumination spectra,
   wherein the imager to simultaneously receive the radiation reflected from the target by illumination from the first, second and third types of illumination sources, and to capture a third image simultaneously with the first and the second images,
   wherein the array further comprising a third type of light sensitive element having a third sensitivity spectrum differing from the first and the second sensitivity spectra, the third type of light sensitive element being responsive to the third illumination spectrum,
   wherein the value of FWHM of the third illumination spectrum is less than value of FWHM of the third sensitivity spectrum,
   and wherein the value of center wavelength and of FWHM of the third illumination spectrum is such that an overlap between the third sensitivity spectrum and the third illumination spectrum is larger than an overlap between the third sensitivity spectrum and the other illumination spectrum.

5. The in-vivo imaging device according to claim 4, wherein the overlap between the third sensitivity spectrum and the third illumination spectrum is greater or equal to five times the overlap between the third sensitivity spectrum and the other illumination spectra.

6. The in-vivo imaging device according to claim 4, wherein the array is a planar array.

7. The in-vivo imaging device according to claim 4, wherein the array is a mosaic array.

8. The in-vivo imaging device according to claim 7, wherein the light sensitive elements are arranged in repeating groups of four.

9. The in-vivo imaging device according to claim 8, wherein each group comprises four adjacent light sensitive elements made up of two green light sensitive elements, one red light sensitive element and one blue light sensitive element.

10. The in-vivo imaging device according to claim 4, wherein the center wavelength of the third illumination spectrum of being greater than center wavelength of the third sensitivity spectrum.

11. The in-vivo imaging device according to claim 1, wherein the center wavelength of the first illumination spectrum are less than center wavelength of the first sensitivity spectrum.

12. The in-vivo imaging device according to claim 1, wherein the center wavelength of the second illumination spectrum of being greater than center wavelength of the second sensitivity spectrum.

13. The in-vivo imaging device according to claim 1, comprising a swallowable capsule.

14. An in-vivo imaging device for narrow band imaging comprising:
   a plurality of narrow band illumination sources having non-overlapping corresponding illumination spectra; and
   an imager comprising a plurality of light sensitive elements covered by wavelength sensitive filters and having differing corresponding sensitivity spectra arranged in a mosaic array for capturing a plurality of narrow band images simultaneously,
   wherein each of the plurality of light sensitive elements is responsive to a corresponding illumination spectra,
   wherein values of full width half maximum (FWHM) of each of the plurality of illumination spectra is less than the corresponding values of FWHM of sensitivity spectra, respectively, and
   wherein values of FWHM of each of the plurality of illumination spectra are such that for each pair of corresponding illumination source and light sensitive element, an overlap between sensitivity spectrum of the light sensitive element and the corresponding illumination spectrum is larger than overlaps of the sensitivity spectrum and illumination spectra of other illumination sources.

15. The in-vivo imaging device according to claim 14, wherein the plurality of narrow band illumination sources includes at least two types of narrow band illumination sources.

16. The in-vivo imaging device according to claim 14, wherein the plurality of light sensitive elements includes at least three different types of light sensitive elements, each type being responsive to a narrow band illumination source having a given illumination spectrum.

17. The in-vivo imaging device according to claim 15, wherein the light sensitive elements are arranged in groups of four and wherein each group comprises four adjacent light sensitive elements made up of two green light sensitive elements, one red light sensitive element and one blue light sensitive element.

18. A method for providing a plurality of narrow band images of an in-vivo target area by an in-vivo imaging device, the method comprising:
   simultaneously illuminating the target area by a plurality of narrow band illumination sources of light radiation having non-overlapping corresponding illumination spectra; and
   capturing the plurality of narrow band images simultaneously based on simultaneously receiving radiation reflected from the target area by an imager comprising an array of a plurality of light sensitive elements covered by wavelength sensitive filters and having differing corresponding sensitivity spectra,
   wherein each of the plurality of light sensitive elements is responsive to a corresponding illumination spectra, wherein values of full width half maximum (FWHM) of each of the plurality of illumination spectra are less than the corresponding values of FWHM of sensitivity spectra, respectively, and wherein values of FWHM of each of the plurality of illumination spectra are such that for each pair of corresponding illumination source and light sensitive element, an overlap between sensitivity spectrum of the light sensitive element and the corresponding illumination spectrum is larger than overlaps of the sensitivity spectrum and illumination spectra of other illumination sources.

19. The method of claim 18, wherein for each of the plurality of light sensitive elements, the overlap between the sensitivity spectrum of the light sensitive element and the corresponding illumination spectrum is greater or equal to five times the overlap between the sensitivity spectrum and the other illumination spectra.

20. The method of claim 18, wherein the array is a planar array.

21. The method of claim 18, wherein the array is a mosaic array.

22. The method of claim 21, wherein each group comprises four adjacent light sensitive elements made up of two green light sensitive elements, one red light sensitive element and one blue light sensitive element.

23. The method of claim 21, wherein the light sensitive elements are arranged in repeating groups of four.

24. The method of claim 18, wherein the plurality of narrow band illumination sources includes at least two types of narrow band illumination sources.

25. The method of claim 18, wherein the plurality of light sensitive elements includes at least three different types of light sensitive elements, each type being responsive to a narrow band illumination source having a given illumination spectrum.

\* \* \* \* \*